United States Patent [19]

Takashima et al.

[11] Patent Number: 5,396,895
[45] Date of Patent: Mar. 14, 1995

[54] APPARATUS FOR SIMULATING BLOOD CIRCULATION

[75] Inventors: Mitsuru Takashima; Yoshiki Satoh, both of Tokyo, Japan

[73] Assignee: Sony Corporation, Japan

[21] Appl. No.: 52,605

[22] Filed: Apr. 27, 1993

Related U.S. Application Data

[62] Division of Ser. No. 851,662, Mar. 16, 1992.

[30] Foreign Application Priority Data

Mar. 18, 1991 [JP] Japan .................................. 3-077269

[51] Int. Cl.6 ................................................ A61B 5/00
[52] U.S. Cl. ...................................... 128/687; 128/672; 434/268; 434/272
[58] Field of Search ................ 434/262, 265, 267, 268, 434/272, 126; 73/865.8, 866.4; 128/672, 687, 697

[56] References Cited

U.S. PATENT DOCUMENTS 2,556,043  6/1951  Roucka ................. 434/268
3,704,528 12/1972  Lewis .................. 434/268

OTHER PUBLICATIONS

Blood Circulation system simulator–uses monitoring unit to record pressure, flow and volume of introduced liquid, Oct. 1987.

Primary Examiner—William E. Kamm
Assistant Examiner—Brian M. Green
Attorney, Agent, or Firm—Ronald P. Kananen

[57] ABSTRACT

An apparatus simulating blood circulation in the human body which allows sphygmic diagnosis simulation to be performed by measuring simulated arterial pulses along a simulated artery portion which simulates an artery portion leading to either the left or right hand of the blood circulating system of the human body. The simulated artery portion is included in a simulated blood circulating passage formed by a layout of tubes representative of the human circulatory system. Each tube has a circular section of rubber resin made of both silicon and natural rubbers in which the wall thickness of the tube, Young Modulus, tensile strength, dimension, and compliance are predetermined to simulate the human body. Sphygmic diagnosis simulation can be performed by measuring the simulated arterial pulses at three points along of a radial artery portion corresponding to three positions of shun, khan, and shaku of the sunko as in the practice of Oriental medicine. Three pressure sensors may be used to detect the simulated pulses and blood circulation at the shun, khan, and shaku spots of the sunko. Information on blood viscosity, artery hardness, and inner wall condition is also obtained.

44 Claims, 8 Drawing Sheets

APPARATUS FOR SIMULATING BLOOD CIRCULATION

This application is a division of application Ser. No. 07/851,662, filed Mar. 16, 1992.

BACKGROUND OF THE INVENTION

(a) Field of the Invention

The present invention relates to an observation apparatus, and in particular to an apparatus for observing the blood circulating function of a patient with no contact with the blood by observing the waveform of the arterial pulses.

(b) Prior Art

Cardiographic or ultrasonic tomographic diagnosis apparatus has heretofore been used for examination of heart disease.

Since the arterial pulses related with the motion of the heart contain important information representative of the condition of the blood circulating function, they are widely used for determining whether or not the blood circulating function is good. Observation of the volumetric pulses representative of the content of blood in the capillary vessels has generally been conducted.

A method of converting changes in pressure due to the heart beat into electrical signals by using a piezoelectric element or capacitor microphone and a method for optically detecting changes in the amount of blood flow by using optical modulating action of hemoglobin in blood have been adopted for detecting the arterial pulses.

In the Oriental medicine, the conditions of a patient are determined by sphygmic diagnosis solely relying on the sense of touch of the arterial pulses on the "sunko", that is, the processus styloideus radii on the inner side of the wrist. In the sphygmic diagnosis of the Oriental medicine, the pulses on the "sunko" are classified into those on three spots, such as upper, middle and lower spots which are referred to as "shun", "khan" and "shaku", respectively and two kinds of pulsation condition "myakki" on the pulse route "keimyaku" appeared on respective spots are sensed.

The term "shun" means the distal end side of the artery of the wrist. The pulses on the "shun" represent the health conditions of the patient from the head to the chest. The term "khan" means the middle artery of the wrist between the distal end and the heart. The pulses on the "khan" represents the health conditions between the chest and the navel. The term "shaku" means the heart side of the artery in the wrist and the pulses on the "shaku" represents the health conditions between the navel and the toe.

A sphygmic diagnosis apparatus in which arterial pulses are detected from the artery of a human being by means of sensors such as an infra-red ray sensor or a pressure sensor for performing the diagnosis by observation of the sphygmogram has heretofore been known as is disclosed in the specification of the Japanese Examined Patent Publication No. 57-52054.

The disclosed diagnosis apparatus comprises three pressure sensor 51, 52 and 53 for converting the arterial pulses on the three spots such as "shun", "khan" and "shaku" of the "sunko" into electrical signal waves and a cuff band 55 which is mounted on the wrist 54 of a patient for biasing the pressure sensors 51, 52 and 53 upon the artery of the wrist as shown in FIG. 1.

The pressure sensors 51, 52 and 53 are disposed on the wrist 54, that is, on and along the artery in the "sunko" and the cuff 55 is wrapped around the wrist. A compressed air is pumped into an air bag (not shown) provided on the cuff 55 from a pneumatic pump via a conduit 56. The arterial pulses can be measured by adjusting the amount of the pumped air to change the pressure applied upon the artery.

The pressure sensors 51, 52 and 53 comprise, for example, so-called electrostatic microphones or piezoelectric microphones. Specifically, in case of the electrostatic microphone, a high d.c. voltage is applied across an electrode of a vibrating plate and a fixed electrode of the vibrating plate is brought into direct contact with a spot on which a pressure is detected, for example the artery of the "sunko". The spacing between the electrode of the vibrating plate and the fixed electrode is changed due to pressure to change the electrostatic capacity therebetween. The voltage generated at this time is detected. The pressure sensors 51, 52 and 53 are connected with an electromagnetic oscillograph and the like through connection codes 51a, 52a and 53a respectively so that the measured arterial pulses are recorded on a recording paper and the like for observing the sphygmogram.

Although the cardiography or ultrasonic tomography has been used for examination of heart disease as mentioned above, it is very hard to quantitatively diagnose the condition of the heart disease by observing the condition of the blood circulating function with no contact with the blood. Confirmation of an abnormality has been visually carried out by well experienced medical docters.

There has been no means for measuring the viscosity of the blood in the artery which is changed by the disease of the internal organs such as heart disease or liver disease except for the blood circulating function for examining the heart disease. Information on the viscosity of blood can not be used for diagnosis of the disease of the internal organs.

It is hard to observe the hardness of the artery, which changes with an advance in the heart disease, with no contact with the blood. A method of estimating the hardness of the artery by pressing a sensor for investigating the relation between stress and strain upon the radial artery has been known as a method of measuring the hardness of the artery without contacting blood. However, this method is strongly influenced by the tissue between the artery and the upper skin. Accordingly, this method is inaccurate so that the hardness of the artery can not be quantified.

OBJECT AND SUMMARY OF THE PRESENT INVENTION

Therefore, the present invention was made in view of such circumstances.

It is a first object of the present invention to provide a blood circulating function observing apparatus which is capable of properly determining the condition of the blood circulating function of a patient in with no contact with the patient's blood.

It is a second object of the present invention to provide a blood viscosity observing apparatus which is capable of properly observing the viscosity of the blood in the artery of a patient in with no contact with the patient's blood.

It is a third object of the present invention to provide an artery hardness observing apparatus which is capable of properly observing the hardness of the artery of a patient with no contact with blood without any experience.

DESCRIPTION OF EMBODIMENTS

An embodiment of a blood circulating function observing apparatus of the present invention will be described in detail with reference to the drawings.

Figure 1:
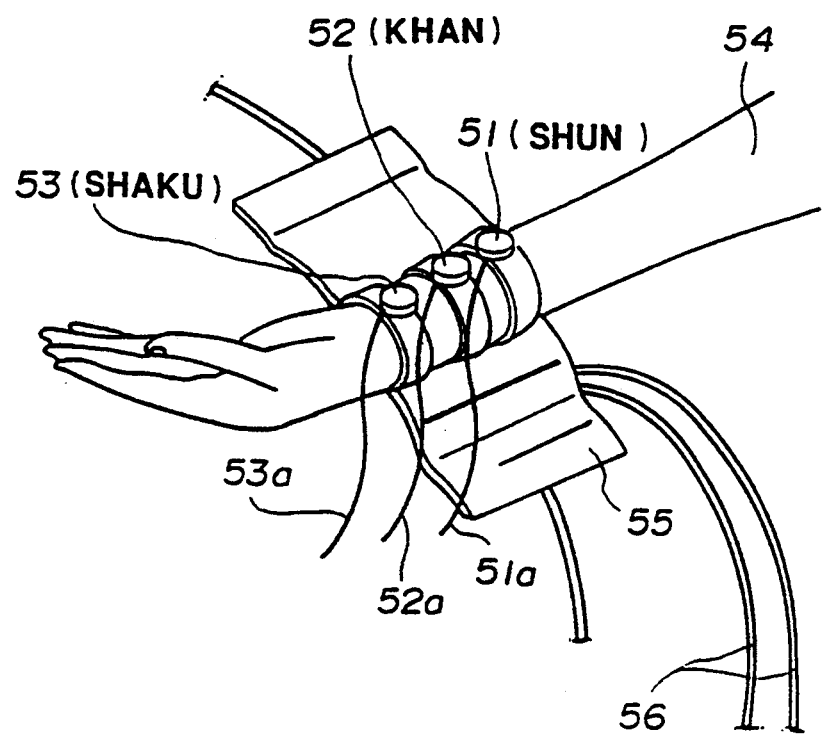
FIG. 1 is a perspective view showing a vascular wave detecting means for detecting the pulses of the shun, khan and shaku of the sunko in the Oriental medicine.
Figure 2:
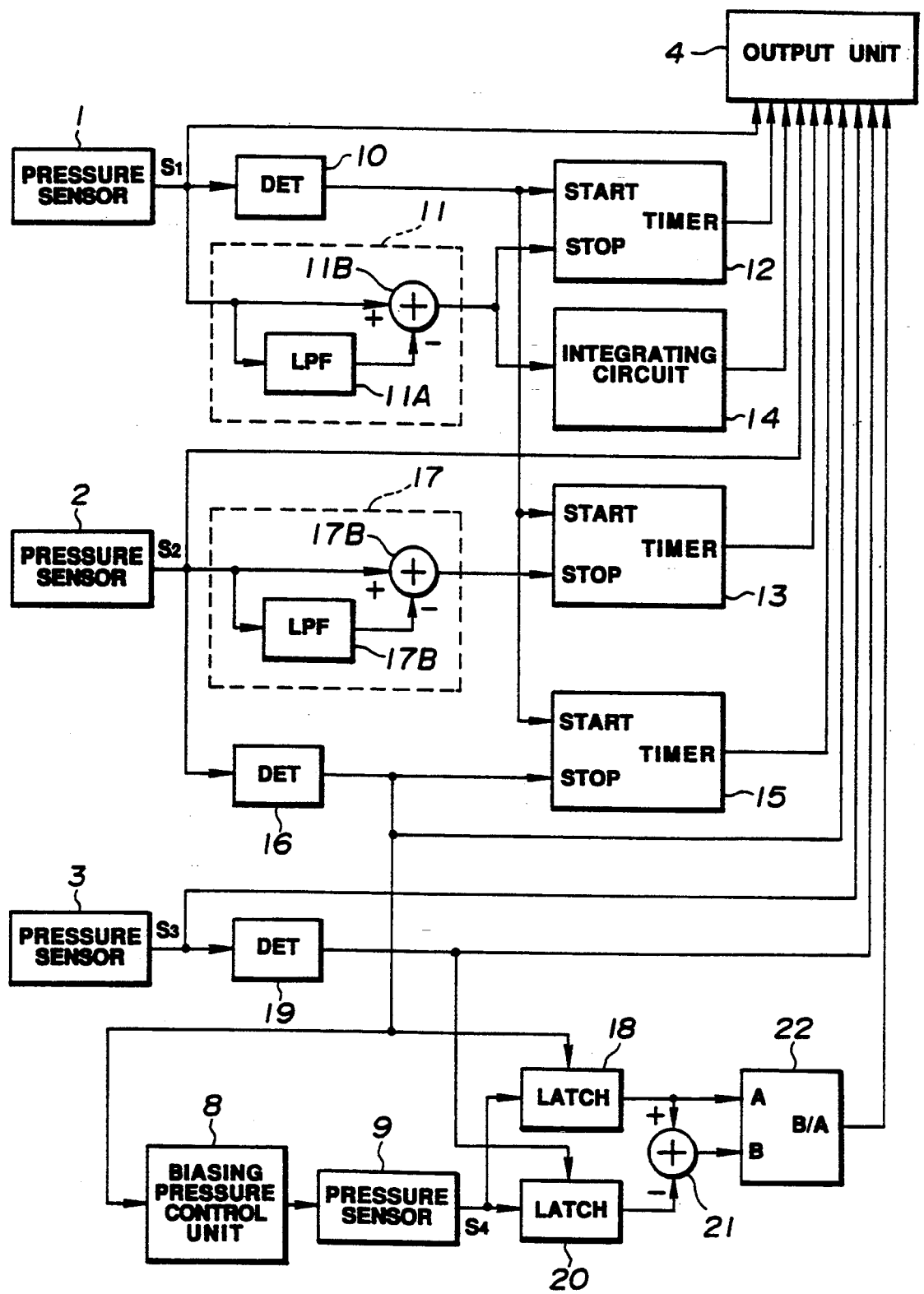
FIG. 2 is block diagram showing the structure of a sphygmic diagnosis apparatus in accordance with the present invention.

The blood circulating function observing apparatus of the present invention is formed as shown in FIG. 2.

The blood circulating function observing apparatus of the present invention is applied to a sphygmic diagnosis apparatus which determines the disease of a patient by detecting the arterial pulses at spots such as "shun", "khan", "shaku" of "sunko" in Oriental medicine. The observing apparatus comprises first to third pressure sensors 1, 2 and 3 which detect the arterial pulses of "shun, "khan", "shaku" of the sunko and convert them into electrical signals. Output signals $S_1$, $S_2$ and $S_3$ from the pressure sensors 1, 2 and 3 are supplied to an output unit 4 for observing the waveforms of the detection output signals $S_1$, $S_2$ and $S_3$. The output unit 4 may be a display for displaying the waveforms of the signals $S_1$, $S_2$ and $S_3$ on a screen or a printer for printing the waveforms of the detected output signals $S_1$, $S_2$ and $S_3$ on a recording paper.

Figure 3:
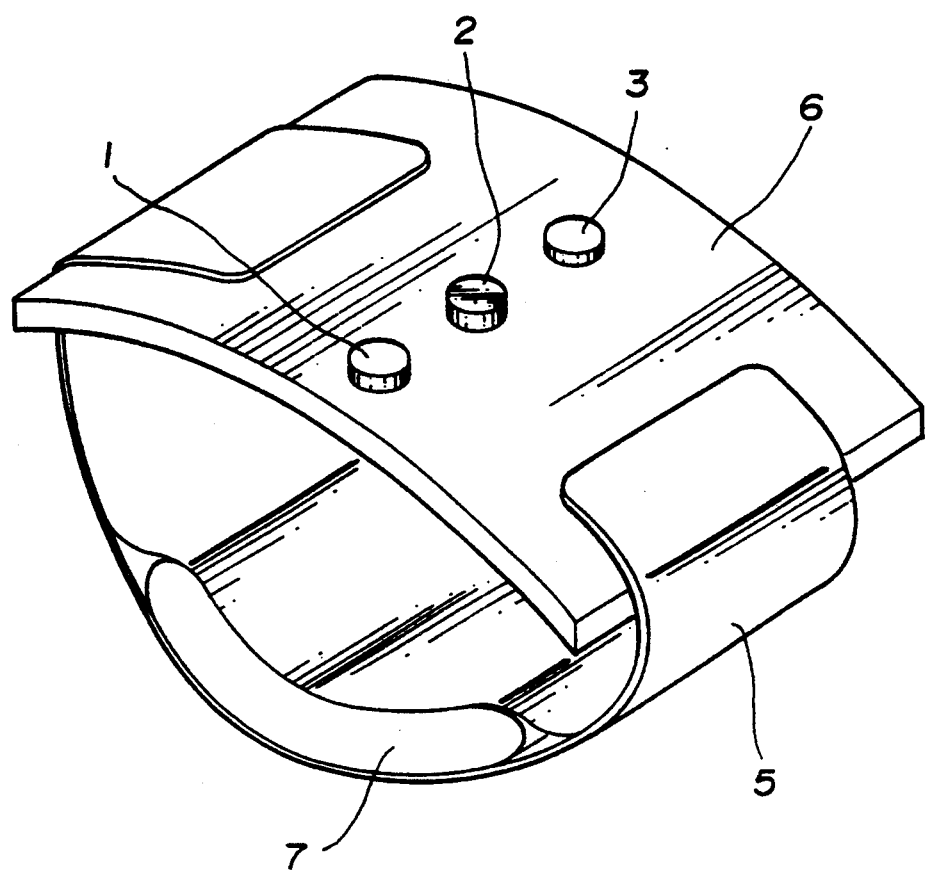
FIG. 3 is a perspective view showing the disposition of three pressure sensors in the sphygmic diagnosis apparatus shown in FIG. 2.
Figure 4:
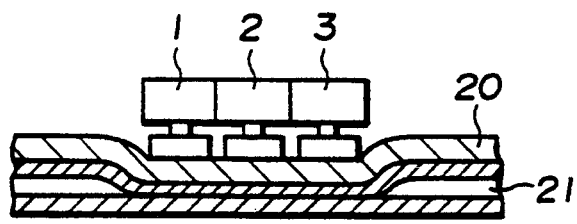
FIG. 4 is a sectional view showing the biasing upon the artery by the three pressure sensors in the sphygmic apparatus shown in FIG. 2.

The first to third pressure sensors 1, 2 and 3 comprise pressure-electric converting elements such as piezoelectric microphones for detecting the arterial pulses of the shun, khan and shaku of the sunko as changes in pressure. The first to third pressure sensors 1, 2 and 3 are disposed on the inner wall of a fixing plate 6 having opposite ends which are connected each other via a cuff band 5 which will be worn around the wrist of a patient as shown in FIG. 3. The first to third pressure sensors 1, 2 and 3 are pressed upon the positions of detection corresponding to the shun, khan and shaku of the sunko in Oriental medicine by the admission of air into an air bag 7 provided on the cuff band 5 for pressing a skin tissue 20 of the wrist of the patient to block an artery 21.

Air is charged into or from the air bag 7 provided in the cuff band 5 from an air pump (not shown) which is controlled by a biasing control unit 8 and the air is discharged via an exhaust valve (not shown) which is controlled by the biasing control unit 8. The biasing pressure supplied by the first to third pressure sensors 1, 2 and 3 of the air bag 7 are detected by a fourth pressure sensor 9.

The first pressure sensor 1 which detects the shun of the sunko, i.e. the artery pulse on the side of the heart, supplies the detection output signal $S_1$ to the output unit 4 and to a first level detecting circuit 10 and a notch detecting circuit 11.

The first level detecting circuit 10 detects when the detection output signal $S_1$ from the first pressure sensor 1 assumes a predetermined output level. A detection output signal from the first level detecting circuit 10 is supplied to first and third timer circuit 12 and 15 as a timer start signal.

The first notch detecting circuit 11 detects a notch (omitted portion of the waveform) contained in the arterial pulses on the side of the heart, i.e. in the detection output signal $S_1$ from the first pressure sensor 1. The first notch detecting circuit 11 comprises a low pass filter 11A for extracting a fundamental wave component of the detection output signal $S_1$ from the first pressure sensor 1 and a subtracter 11B for subtracting the fundamental wave component extracted by the low pass filter 11A from the detection output signals of the first pressure sensor 1. A first notch signal which is obtained as the subtraction output signal from the subtracter 11B is supplied to the first timer circuit 12 as a timer stop signal and to an integrating circuit 14 and to a second timer circuit 13 as a timer start signal.

The first timer circuit 12 measures a period of time from when the first level detecting circuit 10 detects that the detection output signal $S_1$ having a level higher than a predetermined level is obtained until the first notch detecting circuit 11 detects the notch contained in the detection output signal $S_1$ from the first pressure sensor 1. A measurement output signal from the first timer circuit 12 is supplied to the output unit 4. The integrating circuit 14 integrates the first notch detection signal from the first notch detecting circuit 11. The integration output signal from the integrating circuit 14 is supplied to the output unit 4.

The second pressure sensor 2 which detects the khan of the sunko, i.e. the artery pulse between the heart and peripheral side supplies the detection output signal $S_2$ to the output unit 4 and to a second level detecting circuit 16 and a notch detecting circuit 17.

The second level detecting circuit 16 detects when the detection output signal $S_2$ from the second pressure sensor 2 reaches a predetermined output level. An output signal from the second level detecting circuit 16 is supplied to the output unit 4 and the biasing control unit 8 and to a third timer circuit 15 as a timer stop signal and to a first latch circuit 18 as a first latch signal.

The third timer circuit 15 measures a period of time from when the first level detecting circuit 10 detects that the detection output signal $S_2$ having a level higher than a predetermined level is obtained until the second level detecting circuit 10 detects that the detection output signal $S_2$ higher than a predetermined level is obtained from the second pressure sensor 2. A measurement output signal from the third timer circuit 15 is supplied to the output unit 4.

The second notch detecting circuit 17 detects a notch (omitted portion of the waveform) contained in the detection output signal $S_2$ from the second pressure sensor 2, i.e. in the arterial pulses between the heart and the peripheral sides. The second notch detecting circuit 17 comprises a low pass filter 17A for extracting a fundamental wave component of the detection output signal $S_2$ from the second pressure sensor 2 and a subtracter 17B for subtracting the fundamental wave component extracted by the low pass filter 17A from the detection output signal $S_2$ of the second pressure sensor 2. A second notch signal which is obtained as the subtraction output signal from the subtracter 17B is supplied to a second timer circuit 13 as a timer stop signal.

The second timer circuit 13 measures the period of time from when the first notch detecting circuit 11 detects a notch contained in the detection output signal $S_1$ from the first pressure sensor 1 until the second notch detecting circuit 17 detects a notch contained in the detection output signal $S_2$ from the second pressure sensor 2. A measurement output signal from the second timer circuit 13 is supplied to output unit 4.

The third pressure sensor 3 which detects the shaku of sunko, i.e. the arterial pulse on the peripheral side supplies the detection output signal $S_3$ to the output unit 4 and to a third level detecting circuit 19.

The third level detecting circuit 19 detects when the detection output signal $S_3$ from the third pressure sensor 3 reaches a predetermined output level. The detection output signal from the third level detecting circuit 19 is supplied to a second latch circuit 20 as a second latch signal.

The fourth pressure sensor 9, which detects the biasing forces of the first to third pressure sensors 1, 2 and 3 excepted by the air bag 7, supplies the detection output signal $S_4$ to the first and second latch circuits 18 and 20.

The first latch circuit 18 latches the detection output signal $S_4$ from the fourth pressure sensor 9 in response to the first latch signal, i.e. the detection output signal from the second level detecting circuit 16 and supplies the latch output signal to a subtracter 21 and a divider 22. The latch output signal from the first latch circuit 18 represents the blood flow full passage pressure $P_1$ at which the detection output signal $S_2$ not less than a predetermined level is obtained from the second pressure sensor 2.

The second latch circuit 20 latches the detection output signal $S_4$ from the fourth pressure sensor 9 in response to the second latch signal, i.e. the detection output signal from the third level detecting circuit 19 and supplies the latch output signal to a subtracter 21. The latch output signal from the second latch circuit 20 represents the blood flow full passage pressure $P_2$ at which the detection output signal $S_3$ not less than a predetermined level is obtained from the third pressure sensor 3.

The subtracter 21 subtracts the latch output signal from the second latch circuit 20 from the latch output signal from the first latch circuit 18 and supplies the subtraction output signal to the divider 22. The subtraction output signal from the subtracter 21 represents a pressure difference $P_1 - P_2$ which is a difference between the blood flow full passage pressure $P_1$ at which the blood fully passes through the first pressure sensor 1 represented by the latch output signal from the first latch circuit 18 and the blood flow full passage pressure $P_2$ at which the blood fully passes through the second pressure sensor 2 which is represented by the latch output signal from the second latch circuit 20.

The divider 22 normalizes the pressure difference $P_1 - P_2$ which is represented by the subtraction output signal by dividing the subtraction output signal of the subtracter 21 by the latch output signal from the first latch circuit 18. The detection output signal from the division output signal from the divider 22, i.e. the normalized pressure difference $(P_1 - P_2)/P_1$ from the divider 22 is supplied to the output unit 4.

The sphygmic diagnosis apparatus which is formed in such a manner is used in selected one of first to third operative modes.

In the first operation mode, the biasing force of the first to third pressure sensors 1, 2 and 3 by the air bag 7 is gradually changed from the blood flow blocked condition to the full passage condition by controlling a pneumatic pump and an exhaust valve (not shown) by the biasing pressure control unit 8. The waveshape of each of the detection output signals $S_1$, $S_2$ and $S_3$ of the first to third pressure sensors 1, 2 and 3 is observed. Accordingly, the disease of the patient can be diagnosed by observing the arterial pulses of the shun, khan and shaku of the sunko in Oriental medicine.

Figure 5:
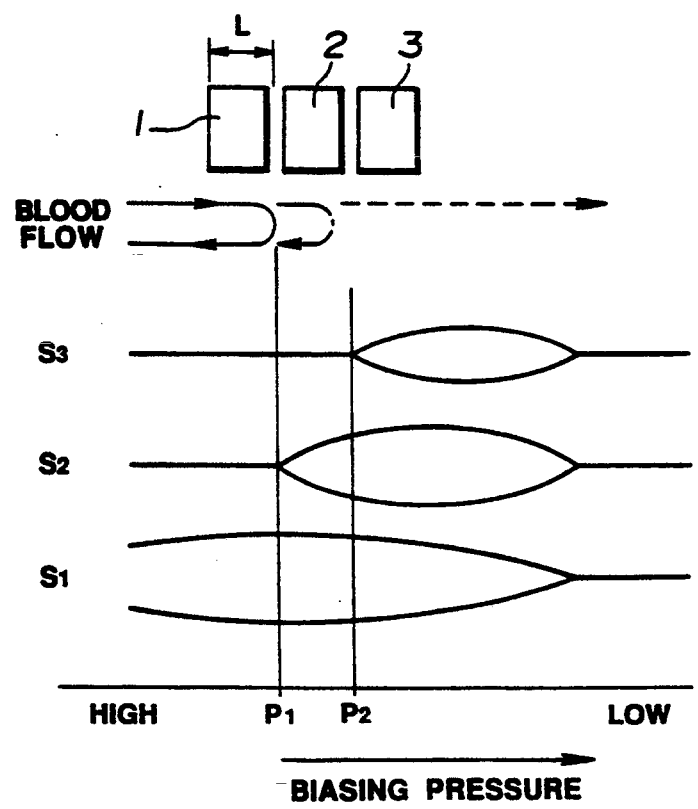
FIG. 5 is a graph showing the changes in the levels of the detection output signals which are obtained by the three pressure sensors in the sphygmic diagnosis apparatus shown in FIG. 2.

If the biasing force of the first to third pressure sensors 1, 2 and 3 exerted by the air bag 7 is gradually changed from the blood flow blocked condition to the full passage condition, the level of the detection output signal $S_1$ of the first pressure 1 which is located on the side of the heart is first elevated and then the level of the detection output signal $S_2$ of the second pressure sensor 2 which is located in the intermediate position is elevated and finally the level of the detection output signal $S_3$ of the third pressure sensor 3 which is located in the terminal position is elevated as shown in FIG. 5. If the biasing force is lowered, the levels of the detection output signals $S_1$, $S_2$ and $S_3$ of the first to third pressure sensors 1, 2 and 3 are simultaneously lowered.

In the second operation mode, the biasing force of the first to third pressure sensors 1, 2 and 3 exerted by the air bag 7 is gradually lowered from the blood flow blocked condition and the pneumatic pump and the exhaust valve (not shown) are controlled by the biasing force control unit 8 in response to the detection output signal from the second level detecting circuit 16 so that the biasing pressure $P_1$ is maintained constant on a blood flow passage restricted condition on which the detection output signal can be obtained from the second level detecting circuit 16.

Figure 6:
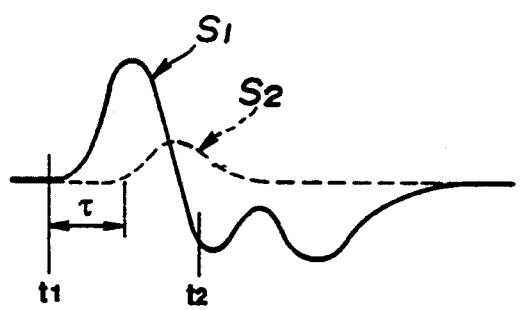
FIG. 6 is a waveform chart showing the waveforms of the detection output signals obtained by the first and second pressure sensors in the sphygmic diagnosis apparatus shown in FIG. 2.

On the blood flow passage restricted condition, each of the detection output signals $S_1$ and $S_2$ obtained by the first and second pressure sensors 1 and 2 have a smooth continuous sinusoidal waveform from the $t_1$ when the ventricle of the heart begins to contract to the time $t_2$ when the aorta valve closes as shown in FIG. 6 in which the waveforms of the detection output signals $S_1$ and $S_2$ of the first and second pressure sensors 1 are depicted by the solid dotted lines, respectively if the blood circulating function of the patient is normal.

Figure 7:
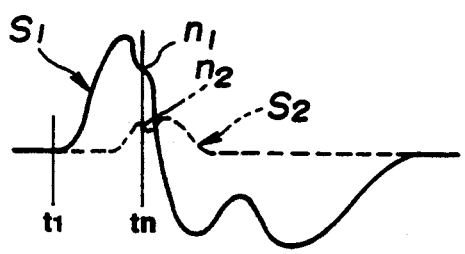
FIG. 7 is a waveform chart showing the wave form representative of an abnormality in pressure of the blood circulating function observed in the sphygmic diagnosis apparatus shown in FIG. 2.
Figure 8:
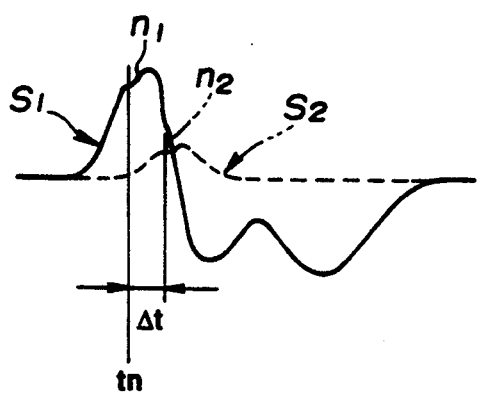
FIG. 8 is a wave form chart showing the wave form representative of an abnormality in blood flow of the blood circulating function observed in the sphygmic diagnosis apparatus shown in FIG. 2.

In contrast to this, the blood circulating function of the patient is abnormal, a notch occurs at an interval from the time $t_1$ when the ventricle of the heart begins to contract and the time $t_2$ when the aorta valve closes. If there is an abnormality of the fast pressure propagation due to valve abnormality, notches $n_1$ and $n_2$ appear at the substantially same time $t_n$ as shown in FIG. 7 in which the waveforms of the detection output signals $S_1$ and $S_2$ are depicted by the solid and dotted lines, respectively. If there is an abnormality of the slow propagation flow due to abnormality in the heart muscle, notches $n_1$ and $n_2$ appear at times having a time difference $\Delta t$ therebetween as shown in FIG. 8 in which the waveforms of the detection output signals $S_1$ and $S_2$ of the first and second pressure sensors 1 and 2 are depicted by solid and dotted lines, respectively When the present sphygmic diagnosis apparatus is in the second operation mode, first timer circuit 12 measures the period of time $t_n$ from the time $t_1$ when the ventricle of the heart begins to contract until the notch $n_1$ appears in the detection output signal $S_1$ of the first pressure sensor 1 and the second timer circuit 13 measures the period of time since the notch $n_2$ appears in the detection output signal of the first pressure sensor 1 until the notch $n_2$ appears in the detection output signal $S_2$ of the second pressure sensor 2, i.e. the time difference $\Delta t$ of the notches $n_1$ and $n_2$ and the output unit 4 outputs the time information $t_n$ and $\Delta t$ of the notches $n_1$ and $n_2$.

The measurement data $t_n$, $\Delta t$ of the first and second timer circuits 12 and 13 are outputted from the output unit 4 as blood flow circulating function observing data in such a manner. Therefore, the blood circulating function condition of the patient can be properly diagnosed in non-contact with blood without any experiences.

The disease condition can be quantified by determining the size (area) of the notch n by integrating in the integrating circuit 14 the first notch detection signal from the first notch detecting circuit 11 which detects the notch $n_1$ appearing in the detection output signal $S_1$ of the first pressure sensor 1. Diagnosis of the disease can be more properly performed by displaying or printing the integration output signal from the integrating circuit 14 as blood circulating function observing data.

In the second operation mode, the third timer circuit 15 measures the period of time since the first level detector 10 detects that the detection output signal $S_1$ not less that a predetermined level is obtained by the first pressure sensor 1 until the second level detecting circuit 16 detects that the detection output signal $S_2$ not less than a predetermined level is obtained from the second pressure sensor 2, i.e. the time which is taken for the blood to move by a distance L between the first and second pressure sensors 1 and 2.

The velocity v at which the blood moves through the first pressure sensor 1 on the blood flow passage restricted condition is represented by equation 1.

$$V \propto 1/\mu \qquad (1)$$

wherein $\mu$ represents the viscosity of blood.

Since the velocity of the blood depends upon the blood viscosity $\mu$, the viscosity can be estimated by measuring the time $\tau$ which is taken for the blood to move by a distance L between the first and second pressure sensors 1 and 2.

The output unit 4 to which the detection output signal is supplied from the third timer circuit 15 outputs the measurement $\tau$ which is taken for the blood move by a distance L between the first and second pressure sensors 1 and 2 as a measurement data of the blood viscosity $\mu$. Accordingly, information on the blood viscosity which is obtained by normalizing the arterial blood viscosity $\mu$ can be obtained in no contact manner with blood.

Figure 9:
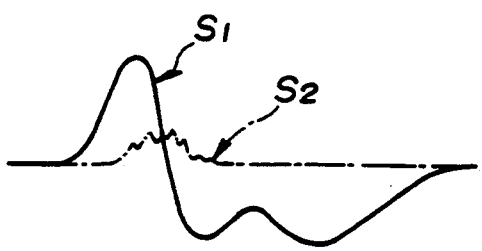
FIG. 9 is a waveform chart showing the wave form representative of the inner wall condition of a blood vessel observed by the sphygmic diagnosis apparatus shown in FIG. 2.

In the second operation mode, the waveforms of a comparison output signal between a reference waveform signal based upon the detection output signal $S_1$ from the first pressure sensor 1 and the detection output signal $S_2$ from the second pressure sensor 2 is displayed or printed out by the output unit 4 as observation information on the condition of the inner wall of the blood vessel the blood which moves through the first pressure sensor 1 on the blood flow passage restricted condition as a thin film flow exhibits a wave surface (representing the elevation and lowering of pressure) depending upon the roughness of the inner wall of the artery. The detection output signal $S_2$ from the second pressure sensor 2 has a waveform depending upon the roughness of the inner wall of the artery as shown in FIG. 9. Accordingly, information on the roughness of the inner wall of the artery can be obtained in a no contact manner with the blood.

In the second operation mode, the waveform of each of the detection output signals $S_1$ and $S_2$ from the first pressure sensor 1 on the heart side and the intermediate second pressure sensor 2 is observed. Since there is provided the third pressure sensor 3 on the peripheral side, accurate waveform observation can be made by removing the influences of the blood on the peripheral side.

In the third operation mode, the pneumatic pump and exhaust valve (not shown) are controlled by the biasing control unit 8 so that the biasing force of the first to third pressure sensors 1, 2 and 3 exerted by the air bag 7 is gradually lowered from the blood flow blocked condition. Information on the normalized pressure difference $(P_1 - P_2)/P_1$ represented by the division output signal from the divider 22 is outputted from the output unit as obtained information on the hardness of the artery.

When the first to third pressure sensors 1, 2 and 3 are closely disposed along the artery in a similar manner to this sphygmic apparatus, loads exerted by the first pressure sensor located on the heart side and the third pressure sensor 3 on the peripheral side give an influence upon the intermediate blood vessel on which the second pressure sensor 2 is located so that the central load increases. The increase in load has a positive correlation with the hardness of artery of the wrist of the patient which biases the first to third pressure sensors 1, 2 and 3. The pressure difference $P_1 - P_2$ between the blood flow full passage pressure $P_1$ at which the blood fully passes through the first pressure sensor 1 on the heart side and the blood full passage pressure $P_2$ at which the blood fully passes through the intermediate second pressure sensor 2 can be used as information representative of the hardness of the artery of the wrist of the patient. Since the blood flow full passage pressure point is a point where the load is balanced with the maximum blood pressure via the skin tissue, the pressure difference $P_1 - P_2$ is hardly influenced by the differences of blood pressure or skin tissues among persons.

In accordance with the present embodiment, the pressure difference $P_1 - P_2$ is displayed or printed out by the output unit 4 as observation information on the hardness of the artery having differences among persons due to blood pressure, etc. by normalizing the pressure difference by the divider 22. Accordingly, observation information on the hardness of the artery can be obtained in a no contact manner with blood.

In accordance with the observing apparatus of the present invention shown in FIGS. 2 to 9, observation of the blood circulating function, the viscosity of the blood, and the hardness of the artery of a patient can be performed in the output unit by observing the waveform of the arterial pulses.

However, information on the arterial pulse in the wrist can not be obtained by techniques relating to an artificial heart and valves therefor which are provided for the simulation device for the human blood circulating system. Simulation of pulses in positions of shun, khan and shaku of the oriental medicine has been impossible. A sphygmic diagnosis simulation blood circulating system which can obtain the arterial pulses will be described with reference to the drawings.

Figure 10:
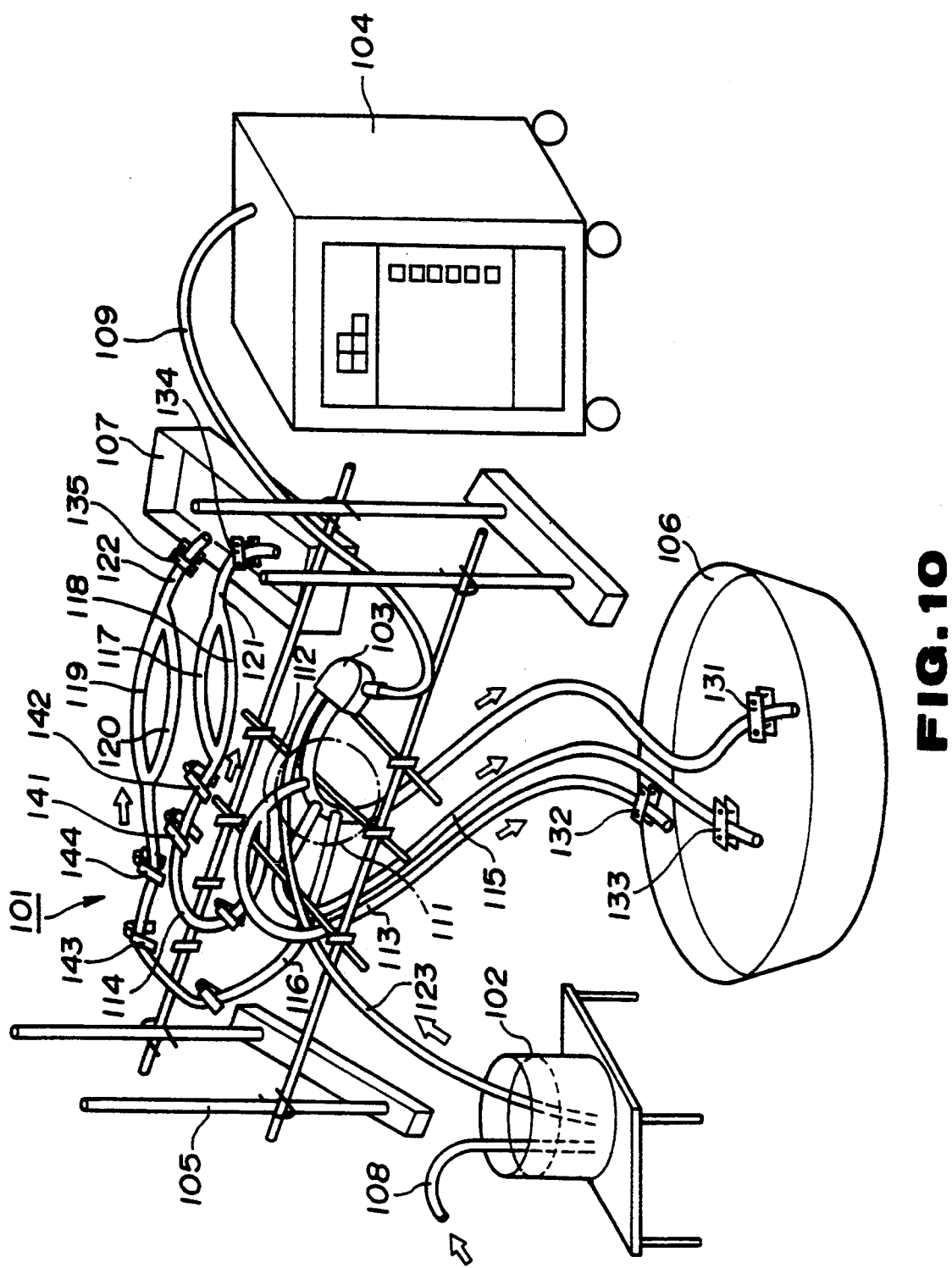
FIG. 10 is a view showing the appearance of a simulated blood circulating apparatus of the present invention.

A simulated blood circulating apparatus comprises a simulated blood circulating passage 101 in which the blood circulating system of a human body is simulated, an atrium portion reservoir 102 for reserving the simulated blood which flows through the simulated blood circulating passage 101, an artificial heart unit 103 for supplying the simulated blood reserved in the atrium portion reservoir 102 to the simulated blood circulating passage 101, and an artificial heart driving unit 104 for driving the artificial heart unit 103 as shown in FIG. 10.

Figure 11:
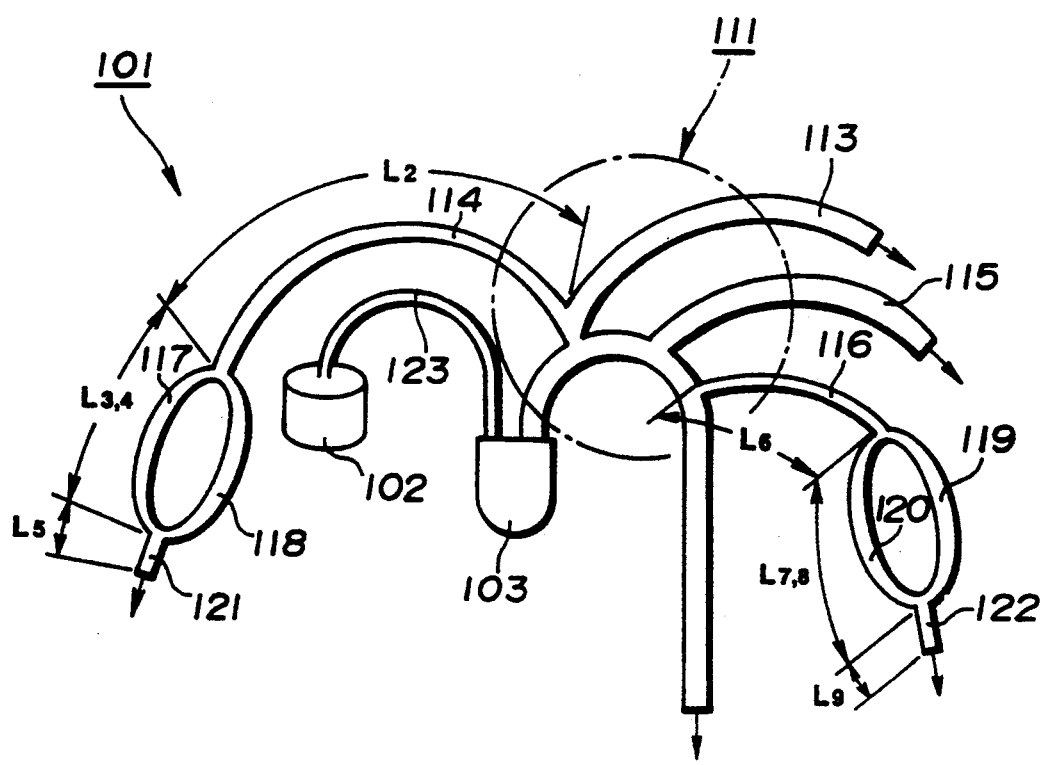
FIG. 11 is a view showing an example of a simulated blood circulating passage of the simulated blood circulating apparatus shown in FIG. 10.
Figure 12:
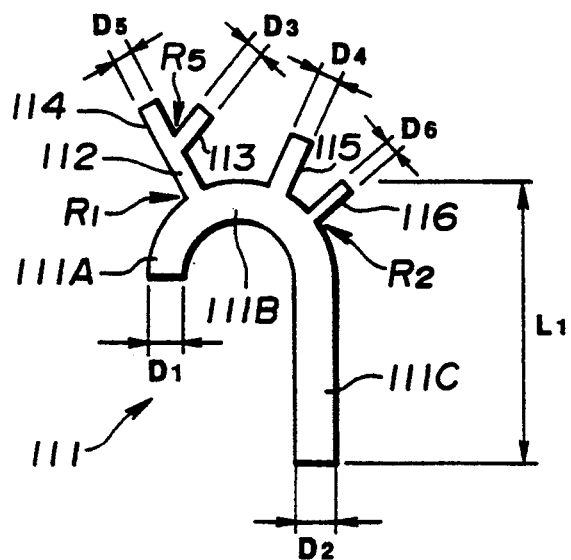
FIG. 12 is a view showing the arch of the aorta portion in the simulated blood circulating passage shown in FIG. 11.
Figure 13:
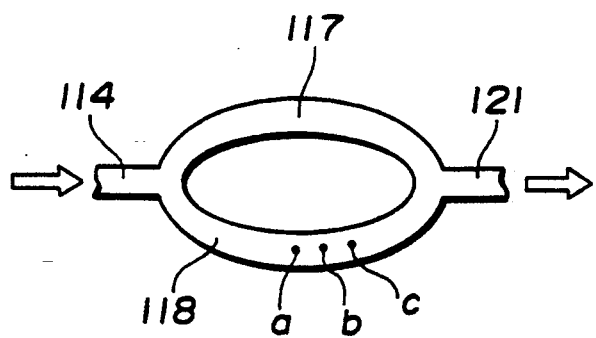
FIG. 13 is a view showing a measuring point where sphygmic diagnosis simulation of Oriental medicine is conducted by the simulated blood circulating apparatus shown in FIG. 10.

The simulated blood circulating passage 101 is formed of tube having circular section of a rubber resin (silicon and natural rubbers) in which the wall thickness of the tube, Young Modulus, tensile strength, dimension and compliance are preset to adapt to simulation of a human body and comprises the arch of the aorta portion 111, the brachiocephalic artery portion 112, the right common carotid artery portion 113, the right subclavian artery portion 114, the left common carotid artery portion 115, the left subclavian artery portion 116, the right ulnar artery portion 117, the right radial artery portion 118, the left ulnar artery portion 119, the left radial artery portion 120, the right hand artery portion 121, and left hand artery portion 122, corresponding to the arch of the aorta, the brachiocephalic, artery, the right common carotid artery, the right subclavian artery, the left common carotid artery, the left subclavian artery, right ulnar artery, the right radial artery, the left ulnar artery, left radial artery, the right hand artery, the left hand artery and the superior and inferior vein, respectively as shown in FIGS. 11 and 12.

In other words, the arch of the aorta portion 111 which is connected with the artificial heart unit 103 comprises a connection portion 111A having an inner diameter $D_1$ of 27.5 mm, a curved portion 111B extending from the connection portion 111A having a curvature radius $R_1$ and a downward depending portion 111C extending from the curved portion 111B and at a curvature radius $R_2$ and having an inner diameter $D_2$ of 17.5 mm. The arch of the aorta 111 are 1.5 mm, 2.0 mm, and 2.5 mm in wall thickness. The length $L_1$ between the top of the curved portion 111B and the lower end of the downward depending portion 111C is 200 mm. The arch of the aorta portion 111 is branched at the curved portion 111B into the brachiocephalic portion 112, the left common carotid artery portion 115 and the left subclavian artery portion 116 and the brachiocephalic portion 112 is branched at the top thereof into the right common carotid artery portion 113 and the right subclavian artery portion 114. The inner diameters $D_3$ and $D_4$ of the right and left common carotid artery portions 113 and 115 are 11 mm. The inner diameter $D_5$ and $D_6$ of the right and left subclavian artery portions 114 and 116 are 8 mm.

The right subclavian portion 114 is formed so that it has a length $L_2$ of 550 mm and is branched at the tip end thereof into the right ulnar artery portion 117 and right radial artery portion 118 which have lengths $L_3$ and $L_4$ of 350 mm, respectively and is connected at the tip ends thereof with the right hand artery portion 121. The length $L_5$ of the right hand artery 121 is 700 mm.

The left subclavian portion 116 is formed so that it has a length $L_6$ of 420 mm and is branched at the tip end thereof into the left ulnar artery portion 119 and left radial artery portion 120 which have lengths $L_7$ and $L_8$ of 350 mm, respectively and is connected at the tip ends thereof with the left hand artery portion 122. The length $L_9$ of left hand artery 122 is 700 mm.

The right subclavian artery portion 114 simulates the right subclavian artery, the auxiliary artery and the brachial artery similarly the left subclavian artery portion 116 simulates the left subclavian artery, the auxiliary artery and the brachial artery. The right ulnar artery portion 117 and right radial artery 118 simulate, at the connection portion with the right hand artery portion 121, the superficial palmer venous arch and the deep palmer arch. Similarly, the left ulnar artery portion 119 and left radial artery portion 120 simulate, at the connection portion with the left hand artery portion 122, the superficial palmer venous arch and the deep palmer arch.

The simulated blood circulating passage 101 having such a structure is supported on a stand 105 in a substantially horizontal manner as shown in FIG. 10. The downward depending portion 111C of the arch of the aorta 111, the right common carotid artery portion 113 and the left common carotid artery portion 115 have respective outlet portions at the tip ends thereof which are introduced into the vein reservoir 106. The right and left hand artery portions 121 and 122 have respective outlet portion at the tip ends thereof, which are introduced into the vein portion reservoir 107. Clips 131, 132, 133, 134 and 135, the gripping forces of which are adjustable by screwing are mounted on the downward depending portion 111C of the arch of the aorta portion 111, the right and left common carotid artery portions 113 and 115, the right and left hand artery portions 121 and 122 in the vicinity of the respective outlets at the tip ends thereof so that the resistances of the respective passages can be variably preset by the clips 131, 132, 133, 134 and 135, respectively. Clips 141, 142 and 143, 144, the gripping forces preset by spring members are mounted on the right and left subclavian artery portions 114 and 116 so that the resistances of the respective passages are preset by the clips 141, 142 and 143, 144, respectively.

The pipe 123 of the simulated blood circulating passage 101 is connected with the artificial heart unit 103 to form a passage for supplying simulated blood reserved in the atrium reservoir 102 to the artificial heart unit 103. The atrium reservoir 102 is replenished with simulated blood via a replenishing pipe 108.

The artificial heart unit 103 is driven by supplying driving compressed air from the artificial heart driving unit 104, the artificial heart unit 103 pumps out simulated blood which is supplied from the atrium reservoir 102 through the pipe 123 into the arch of the aorta portion 111 of the simulated blood circulating passage 101.

In the thus formed simulated blood circulating apparatus, the simulated blood is supplied to the simulated blood circulating passage 101 from the artificial heart unit 103 by driving the artificial heart unit 103. The simulated blood which is supplied to the simulated blood circulating passage 101 is discharged to the vein reservoir 106 from respective outlets at the tip end thereof of the downward depending portion 111C of the arch of the aorta portion 111, the right and left common carotid artery portions 113 and 115 and from the right and left hand artery portions 121 and 122.

The passages of the arch of the aorta portion 111, the right brachiocephalic portion 112, the subclavian artery portion 114 and the right ulnar artery portion 117, the right radial artery portion 118 and the right hand artery portion 121 of the simulated blood circulating passage 101 simulate the artery portion in the right hand of the blood circulating system of the human body. Sphygmic diagnosis simulation can be performed by measuring the arterial pulses at three points a, b and c of the right radial artery portion 118 corresponding to three positions of the shun, khan and shaku of the sunko in Oriental medicine. Similarly, the passages of the arch of the aorta portion 111, the left subclavian artery portion 116 and the left ulnar artery portion 119, the left radial artery portion 120 and the left hand artery portion 122 of the simulate blood circulating passage 101 simulated the artery portion in the left hand of the blood circulating system of the human body. Sphygmic diagnosis simulation can be performed by measuring the arterial pulses at three points a, b and c of the left radial artery portion 120 corresponding to three positions of the shun, khan and shaku of the sunko in Oriental medicine.

As mentioned above, in the blood circulating function observing apparatus of the present invention, a notch contained in the detection output signal from the first pressure sensor which detects the arterial pulses on the heart side is detected by the first notch detecting circuit and a notch contained in the detection output signal from the second pressure sensor which detects the arterial pulses on the peripheral side on the blood flow passage limit condition in which a detection output signal having a predetermined level can be obtained by the second pressure sensor which detects the arterial pulses on the peripheral side. The blood circulating function observation data are obtained as notch occurrence time information and are outputted from the output means. Accordingly, the condition of the blood circulating function of the patient can be properly diagnosed in a noncontact manner with blood without any experience.

In the blood viscosity observing apparatus of the present invention, the blood viscosity observing data which are quantified as the time difference between the time when the detection output signal is obtained by the first pressure sensor which detects the arterial pulses on the heart side and the time detection output signal is obtained by the second pressure sensor which detects the arterial pulses on the peripheral side are obtained and outputted from the output means on the blood flow passing limit condition in which the detection output signal having a predetermined level is obtained by the second pressure sensor which detects the arterial pulses on the peripheral side. Hence the blood viscosity of the patient can be properly diagnosed in a non-contact manner with blood without any experience. Information on the blood viscosity can be used for the diagnosis of the internal organs.

The blood flow passage limitation is conducted at the same pressure in three positions which are closely positioned along the artery in the artery hardness observing apparatus of the present invention. The arterial pulses in the intermediate and peripheral positions of the three biasing positions which are closed disposed along the artery are detected by the first and second pressure sensors, respectively. The biasing force exerted by biasing means to restrict the blood flow is detected by the third pressure sensor. The detection signal representative of the difference in level between the detection output signals which are obtained by the third pressure sensors on the blood flow passage restricted conditions in which the first and second pressure sensors obtain detection output signals having predetermined levels can be obtained as observation information on the quantified hardness of the artery. Since the observation information on the hardness of the artery is outputted from the output means, the hardness of artery of the patient can be properly diagnosed in a non-contact manner with blood without any experience. Accordingly, the information on the hardness of the artery can be used for the diagnosis of the heart disease.

What is claimed is:

1. A simulated blood circulating apparatus for simulating a sphygmic human blood flow through the human circulatory system, comprising:
   an atrium reservoir for holding a supply of simulated blood and for providing said simulated blood to an artificial heart unit;
   said artificial heart unit connected to said atrium reservoir and pumping said simulated blood in response to an artificial heart driving unit to provide volumetric pulses of the simulated blood to a simulated blood circulating passage means;
   wherein, said simulated blood circulating passage means comprises a layout of open-ended tubes connected to one another so as to be representative of the layout of the human circulatory system extending from the heart to at least one hand; said layout of open-ended tubes directing and exerting pressure on said volumetric pulses of said simulated blood traveling therethrough for simulating the flow of a human pulse; and
   said layout of open-ended tubes including artery tubing comprised of at least one tube portion, responsive to said volumetric pulses, through which said volumetric pulses of said simulated blood travel in a single direction of flow.

2. A simulated blood circulating apparatus as defined in claim 1, wherein, said at least one tube portion changes along its length due to the passage of pulses therethrough to simulate the travel of human blood pulses through an artery.

3. A simulated blood circulating apparatus as defined in claim 1, wherein said layout of open-tubes exerts a resistance to said flow, and further including resistance adjusting means for changing the resistance exerted by said layout of said open-ended tubes to the flow of simulated blood through said simulated blood circulating passage means.

4. A simulated blood circulating apparatus as defined in claim 3, wherein, said resistance adjusting means adjustably restricts the flow along said single direction into and out of the at least one tube portion.

5. A simulated blood circulating apparatus as defined in claim 4, wherein, said resistance adjusting means comprise clips for constricting the flow of simulated blood through a tube at said clip, each clip having a screw means for adjusting the resistance to the flow exerted by said tube at said clip.

6. A simulated blood circulating apparatus as defined in claim 1, comprising:
pressure sensing means
for detecting said volumetric pulses of simulated blood.

7. A simulated blood circulating apparatus as defined in claim 6, wherein,
said pressure sensing means comprises pressure sensors disposed along the at least one tube simulating an artery at spots simulating shun, khan, and shaku spots along an artery in Oriental medicine, wherein, said shun, khan, and shaku spots on the sunko correspond substantially to spots on a processus styloideus radii on an inner side of a wrist with said shun spot being on a heart side, said khan spot being between said heart side and a distal end side, and said shaku spot being on said distal end side.

8. A simulated blood circulating apparatus as defined in claim 1, wherein said layout of open-ended tubes of said simulated blood circulating passage means comprises a curved aorta tube simulating the arch of the aorta connected to the artery tubing;
said artery tubing comprises a subclavian artery tube, a radial artery tube, an ulnar artery tube, and a hand artery tube, each tube in said artery tubing means having at least two ends;
wherein, said at least one tube portion of said artery tubing comprises the radial artery tube,
said subclavian artery tube connected at one end to a curve of the curved aorta tube;
said radial artery tube is connected in parallel with the ulnar artery tube, both the radial artery tube and ulnar artery tube have one end connected in common with the other end of the subclavian tube and have their other downstream ends connected in common with said hand artery tube.

9. A simulated blood circulating apparatus as defined in claim 1, wherein said layout of open-ended tubes of said simulated blood circulating passage means comprises a curved aorta tube having a curve for simulating the arch of the aorta connected to a right and a left artery tubing;
said right artery tubing comprises a right subclavian artery tube, a right radial artery tube, a right ulnar artery tube, and a right hand artery tube, each of said tubes having at least two ends;
said left artery tubing comprises a left subclavian artery tube, a left radial artery tube, a left ulnar artery tube, and a left hand artery tube, each of said tubes having at least two ends;
wherein, said at least one tube portion where the simulated blood pulses pass comprises the right radial artery tube and the left radial artery tube,
said right subclavian artery tube connected at one end to a tube juncture located along the curve of the curved aorta tube down from the artificial heart unit and up along said curve of the curved aorta tube from the left subclavian artery tube;
said left subclavian artery tube connected at one end along the curve of the curved aorta tube down from the tube juncture leading to the right subclavian artery tube;
said each right and left radial artery tube is connected in parallel with the respective right and left ulnar artery tube, both the radial artery tube and ulnar artery tube have one end connected in common with the other end of the respective right and left subclavian tube and have their other ends connected in common with a respective right and left hand artery tube.

10. A simulated blood circulating apparatus as defined in claim 9, wherein,
the curve of the aorta tube comprises a circular arc curve;
said tube juncture, a left common carotid artery tube, and the left subclavian artery tube being connected to and sequentially along said curve, wherein, said tube juncture is connected up along said curve towards the artificial heart unit from the left common carotid artery tube and said left common carotid is connected up along said curve towards the artificial heart unit from the left subclavian artery tube;
said tube juncture further comprising a brachiocephalic artery tube having at least two ends, one end being connected to the curve of the aorta tube and the other end to a common connection between the right subclavian artery tube and a right common carotid artery tube.

11. A simulated blood circulating apparatus as defined in claim 10, further comprising:
vein reservoir means for receiving the simulated blood from the right and left common carotid artery tubes, the aorta tube, and the left and right hand artery tubes.

12. A simulated blood circulating apparatus as defined in claim 10, wherein,
diameter of said aorta tube gets progressively smaller away from the end connected to the artificial heart;
the right and left common carotid artery tubes have equal diameters;
the right and left subclavian artery tubes have same diameter which is smaller than the diameter of the common carotid artery tubes; and
all the artery tubes have a diameter smaller than the end of the aorta tube furthest from the artificial heart unit.

13. A simulated blood circulating apparatus as defined in claim 10, further including resistance adjusting means for changing resistance to the flow of simulated blood through each tube of said simulated blood circulating passage means.

14. A simulated blood circulating apparatus as defined in claim 1, wherein:

said layout of open-ended tubes of said simulated blood circulating passage means comprises tubes having a circular section made of rubber resin, whereby each of said tubes have a preset wall thickness, Young Modulus, tensile strength, dimension, and compliance such that changes in the tubes due to the simulated blood pulses passing therethrough in said tubes simulate the changes in an artery in a human circulatory system as human blood pulses pass therethrough.

15. A simulated blood circulating apparatus as defined in claim 1, wherein said at least one tube portion changes at three spots along a length of the at least one tube simulating shun, khan, and shaku spots along an artery in Oriental medicine, wherein, said shun, khan, and shaku spots on a sunko correspond substantially to spots on a processus styloideus radii on the inner side of a wrist with said shun spot being on a heart side, said khan spot being between said heart side and a distal end side, and said shaku spot being on said distal end side.

16. A simulated blood circulating apparatus for simulating a sphygmic human blood flow through the human circulatory system, comprising:
an atrium reservoir for holding a supply of simulated blood;
an artificial heart unit connected to said atrium reservoir to which the simulated blood is supplied from said atrium reservoir;
an artificial heart driving unit connected to said artificial heart unit for driving the artificial heart unit; and
a simulated blood circulating passage means to which the simulated blood is supplied from said artificial heart unit,
wherein, said simulated blood circulating passage means comprises tubing means, arranged in a layout simulating portions of the human circulatory system, including an artery tubing means comprised of at least one tube portion through which volumetric pulses of the simulated blood from the artificial heart unit pass; wherein,
the volumetric pulses of simulated blood passing through said at least one tube portion in said simulated circulatory system simulate human pulses and said at least one tube portion changes due to the passage of pulses therethrough to simulate the travel of human blood pulses through an artery; and
further including resistance adjusting means connected to said artery tubing means for changing the resistance of the flow of simulated blood through said simulated blood circulating passage means;
wherein, said resistance adjusting means comprises clips, each clip gripping the artery tubing means and having a screw means to allow the constriction of the tube by the clip to be adjusted, whereby, said resistance adjusting means adjustably restricts the flow into and out of the at least one tube portion.

17. A simulated blood circulating apparatus for simulating a sphygmic human blood flow through the human circulatory system, comprising:
an atrium reservoir for holding a supply of simulated blood;
an artificial heart unit connected to said atrium reservoir to which the simulated blood is supplied from said atrium reservoir;
an artificial heart driving unit connected to said artificial heart unit for driving the artificial heart unit; and
a simulated blood circulating passage means to which the simulated blood is supplied from said artificial heart unit,
wherein, said simulated blood circulating passage means comprises tubing means, arranged in a layout simulating portions of the human circulatory system, including an artery tubing means comprised of at least one tube portion through which volumetric pulses of the simulated blood from the artificial heart unit pass,
wherein the volumetric pulses of simulated blood passing through said at least one tube portion in said simulated circulatory system simulate human pulses and said at least one tube portion changes due to the passage of pulses therethrough to simulate the travel of human blood pulses through an artery,
wherein said tubing means of said simulated blood circulating passage means comprises a curved aorta tubing means having a curve simulating the arch of the aorta connected to the artery tubing means;
said artery tubing means comprises a subclavian artery tube, a radial artery tube, an ulnar artery tube, and a hand artery tube and each tube of said artery tubing means has at least two ends;
wherein, said at least one tube portion through which the simulated blood pulses pass comprises the radial artery tube,
said subclavian artery tube connected at one end to the curve of the curved aorta tubing means;
said radial artery tube is connected in parallel with the ulnar artery tube, both the radial artery tube and ulnar artery tube have one end connected in common with the other end of the subclavian tube and have their other ends connected in common with a hand artery tube.

18. A simulated blood circulating apparatus as defined in claim 17, further comprising: vein reservoir means for receiving the simulated blood from said tubing means.

19. A simulated blood circulating apparatus as defined in claim 17, wherein,
a diameter of said curved aorta tubing means gets progressively smaller away from the end connected to the artificial heart unit; and
said tubes in said artery tubing means each have a diameter smaller than the end of the aorta tube furthest from the artificial heart unit.

20. A simulated blood circulating apparatus as defined in claim 17, further including resistance adjusting means for changing resistance to the flow of simulated blood through each tube of said simulated blood circulating passage means.

21. A simulated blood circulating apparatus as defined in claim 17, wherein:
said layout of open-ended tubes of said simulated blood circulating passage means comprises tubes having a circular section made of rubber resin, whereby each of said tubes have a preset wall thickness, Young Modulus, tensile strength, dimension, and compliance such that changes in the tubes due to the simulated blood pulses passing therethrough in said tubes simulate the changes in an artery in a human circulatory system as human blood pulses pass therethrough.

22. A simulated blood circulating apparatus as defined in claim 13, wherein said at least one tube portion changes along a length of the tube due to the passage of pulses therethrough to simulate the travel of human blood pulses through an artery.

23. A simulated blood circulating apparatus as defined in claim 17, wherein said at least one tube portion changes at three spots along a length of the at least one tube simulating shun, khan, and shaku points along an artery in Oriental medicine; wherein, said shun, khan, and shaku spots on a sunko correspond substantially to spots on a processus styloideus radii on an inner side of a wrist with said shun spot being on a heart side, said khan spot being between said heart side and a distal end side, and said shaku spot being on said distal end side.

24. A simulated blood circulating apparatus as defined in claim 17, comprising:
pressure sensing means for detecting said volumetric pulses of simulated blood.

25. A simulated blood circulating apparatus as defined in claim 24, wherein
said pressure sensing means comprises three pressure sensors disposed along said at least one tube portion simulating an artery at spots simulating the shun, khan, and shaku spots along an artery in Oriental medicine; wherein, said shun, khan, and shaku spots on a sunko correspond substantially to spots on the processus styloideus radii on an inner side of a wrist with said shun spot being on a heart side, said khan spot being between said heart side and a distal end side, and said shaku spot being on said distal end side.

26. A simulated blood circulating apparatus for simulating a sphygmic human blood flow through the human circulatory system, comprising:
an atrium reservoir for holding a supply of simulated blood;
an artificial heart unit connected to said atrium reservoir to which the simulated blood is supplied from said artrium reservoir;
an artificial heart driving unit connected to said artificial heart unit for driving the artificial heart unit; and
a simulated blood circulating passage means to which the simulated blood is supplied from said artificial heart unit,
wherein, said simulated blood circulating passage means comprises tubing means, arranged in a layout simulating portions of the human circulatory system, including an artery tubing means comprised of at least one tube portion through which volumetric pulses of the simulated blood from the artificial heart unit pass,
wherein, the volumetric pulses of simulated blood passing through said at least one tube portion in said simulated circulatory system simulate human pulses and said at least one tube portion changes due to the passage of pulses therethrough to simulate the travel of human blood pulses through an artery,
wherein said simulated blood circulating passage means comprises a curved aorta tubing means having a curve for simulating the arch of the aorta connected to a right and a left artery tubing means;
said right artery tubing means comprises a right subclavian artery tube, a right radial artery tube, a right ulnar artery tube, and a right hand artery tube;
said left artery tubing means comprises a left subclavian artery tube, a left radial artery tube, a left ulnar artery tube, and a left hand artery tube, each of said tubes having at least two ends;
wherein, said at least one tube portion where the simulated blood pulses pass comprises the right radial artery tube and the left radial artery tube, each of said tubes having at least two ends;
said right subclavian artery tube connected at one end to a tube juncture located along the curve of the curved aorta tubing means down from the artificial heart unit and up along the aorta curve from the left subclavian artery tube;
said left subclavian artery tube connected at one end along the curve of the curved aorta tubing means down from the tube juncture leading to the right subclavian artery tube;
said each right and left radial artery tube being connected in parallel with the respective right and left ulnar artery tube, both the radial artery tube and ulnar artery tube have one end connected in common with the other end of the respective right and left subclavian tube and have their other ends connected in common with a respective right and left hand artery tube.

27. A simulated blood circulating apparatus as defined in claim 26, wherein,
the curve of the curved aorta tubing means comprises a circular arc curve; said tube juncture means, a left common cartid artery tube, and the left subclavian artery tube being connected in sequence along said curve;
wherein, said tube juncture means is connected up from the left common carotid artery tube and said left common carotid artery tube is connected up along said curve towards the artificial heart unit from the left subclavian artery tube;
said tube juncture means further comprising a brachiocephalic artery tube having at least two ends, one end being connected to the curve of the curved aorta tubing means and the other end to a common connection between the right subclavian artery tube and a right common carotid artery tube.

28. A simulated blood circulating apparatus as defined in claim 27, further comprising:
vein reservoir means for receiving the simulated blood from the right and left common carotid artery tubes, the curved aorta tubing means, and the left and right hand artery tubes.

29. A simulated blood circulating apparatus as defined in claim 28, wherein,
a diameter of said curved aorta tubing means gets progressively smaller away from the end connected to the artificial heart;
the right and left common carotid artery tubes have equal diameters;
the right and left subclavian artery tubes have a same diameter, smaller than the diameter of the common carotid arteries; and
all the tubes in said artery tubing means have a diameter smaller than the end of the aorta tube furthest from the artificial heart unit.

30. A simulated blood circulating apparatus as defined in claim 29, further including resistance adjusting means for changing resistance to the flow of simulated blood through each tube of said simulated blood circulating passage means.

31. A simulated blood circulating apparatus as defined in claim 26, further comprising:
vein reservoir means for receiving the simulated blood from said tubing means.

32. A simulated blood circulating apparatus as defined in claim 26, wherein,
the diameter of said aorta tubing means gets progressively smaller away from the end connected to the artificial heart unit; and said tubes in said artery tubing means each has a diameter smaller than the end of the aorta tubing means furthest from the artificial heart unit.

33. A simulated blood circulating apparatus as defined in claim 26, further including resistance adjusting means for changing resistance to the flow of simulated blood through each tube of said simulated blood circulating passage means.

34. A simulated blood circulating apparatus as defined in claim 26, wherein:
said layout of open-ended tubes of said simulated blood circulating passage means comprises tubes having a circular section made of rubber resin, whereby each of said tubes have a preset wall thickness, Young Modulus, tensile strength, dimension, and compliance such that changes in the tubes due to the simulated blood pulses passing therethrough in said tubes simulate the changes in an artery in a human circulatory system as human blood pulses pass therethrough.

35. A simulated blood circulating apparatus as defined in claim 26, wherein said at least one tube portion changes along a length of the at least one tube due to the passage of pulses therethrough to simulate the travel of human blood pulses through an artery.

36. A simulated blood circulating apparatus as defined in claim 26, wherein said at least one tube portion changes at three spots along a length of the at least one tube simulating the shun, khan, and shaku spots along an artery in Oriental medicine;
wherein, said shun, khan, and shaku spots on a sunko correspond substantially to spots on a processus styloideus radii on an inner side of a wrist with said shun spot being on a heart side, said khan spot being between said heart side and a distal end side, and said shaku spot being on said distal end side.

37. A simulated blood circulating apparatus as defined in claim 26, comprising:
pressure sensing means for detecting said volumetric pulses of simulated blood.

38. A simulated blood circulating apparatus as defined in claim 37, wherein,
said pressure sensing means comprises three pressure sensors disposed along said at least one tube portion simulating an artery at spots simulating shun, khan, and shaku spots along an artery in Oriental medicine;
wherein, said shun, khan, and shaku spots on a sunko correspond substantially to spots on a processus styloideus radii on an inner side of a wrist with said shun spot being on a heart side, said khan spot being between said heart side and a distal end side, and said shaku spot being on said distal end side.

39. A simulated blood circulating apparatus for simulating a sphygmic human blood flow through the human circulatory system, comprising:
an atrium reservoir for holding a supply of simulated blood;
an artificial heart unit connected to said atrium reservoir to which the simulated blood is supplied from said atrium reservoir;
an artificial heart driving unit connected to said artificial heart unit for driving the artificial heart unit; and
a simulated blood circulating passage means to which the simulated blood is supplied from said artificial heart unit,
wherein, said simulated blood circulating passage means comprises tubing means, arranged in a layout simulating portions of the human circulatory system, including an artery tubing means comprised of at least one tube portion through which volumetric pulses of the simulated blood from the artificial heart unit pass.
wherein the volumetric pulses of simulated blood passing through said at least one tube portion in said simulated circulatory system simulate human pulses and said at least one tube portion changes due to the passage of pulses therethrough to simulate the travel of human blood pulses through an artery, wherein:
said simulated blood circulating passage means comprises tubes having a circular section made of rubber resin, whereby said tubes have a preset wall thickness, Young Modulus, tensile strength, dimension, and compliance such that changes in the tubes due to the simulated blood pulses passing therethrough in said tubes simulate the changes in an artery in a human circulatory system as human blood pulses pass therethrough.

40. A simulated blood circulating apparatus as defined in claim 39, wherein said at least one tube portion changes along a length of the tube due to the passage of pulses therethrough to simulate the travel of human blood pulses through an artery.

41. A simulated blood circulating apparatus as defined in claim 39, comprising:
pressure sensing means for detecting said volumetric pulses of simulated blood.

42. A simulated blood circulating apparatus as defined in claim 41, wherein,
said pressure sensing means comprises three pressure sensors disposed along said at least one tube portion simulating an artery at spots simulating the shun, khan, and shaku spots along an artery in Oriental medicine;
wherein, said shun, khan, and shaku spots on a sunko correspond substantially to spots on a processus styloideus radii on an inner side of a wrist with said shun spot being on a heart side, said khan spot being between said heart side and a distal end side, and said shaku spot being on said distal end side.

43. A simulated blood circulating apparatus for simulating a sphygmic human blood flow through the human circulatory system, comprising:
an atrium reservoir for holding a supply of simulated blood;
an artificial heart unit connected to said artrium reservoir to which the simulated blood is supplied from said atrium reservoir;
an artificial heart driving unit connected to said artificial heart unit for driving the artificial heart unit; and
a simulated blood circulating passage means to which the simulated blood is supplied from said artificial heart unit, wherein, said simulated blood circulating passage means comprises tubing means, arranged in a layout simulating portions of the human circulatory system, including an artery tubing means comprised of at least one tube portion through which volumetric pulses of the simulated blood from the artificial heart unit pass, wherein, the volumetric pulses of simulated blood passing through said at least one tube portion in said simulated circulatory system simulate human pulses and said at least one tube portion changes due to the passage of pulses therethrough to simulate the travel of human blood pulses through an artery;

wherein, said at least one tube portion changes at three spots along a length of the tube simulating the shun, khan, and shaku spots along an artery in Oriental medicine;

wherein, said shun, khan, and shaku spots on the sunko correspond substantially to spots on the processus styloideus radii on the inner side of a wrist with said shun spot being on a heart side, said khan spot being between said heart side and a distal end side, and said shaku spot being on said distal end side.

44. A simulated blood circulating apparatus for simulating a sphygmic human blood flow through the human circulatory system, comprising:

an atrium reservoir for holding a supply of simulated blood;

an artificial heart unit connected to said atrium reservoir to which the simulated blood is supplied from said atrium reservoir;

an artificial heart driving unit connected to said artificial heart unit for driving the artificial heart unit; and a simulated blood circulating passage means to which the simulated blood is supplied from said artificial heart unit, wherein, said simulated blood circulating passage means comprises tubing means, arranged in a layout simulating portions of the human circulatory system, including an artery tubing means comprised of at least one tube portion through which volumetric pulses of the simulated blood from the artificial heart unit pass, comprising:

pressure sensing means disposed along a tube simulating an artery;

said pressure sensing means detecting said volumetric pulses of simulated blood;

wherein, said pressure sensing means comprises three pressure sensors disposed along said at least one tube portion simulating an artery at spots simulating a shun, khan, and shaku spots along an artery in Oriental medicine;

wherein, said shun, khan, and shaku spots on a sunko correspond substantially to spots on a processus styloideus radii on an inner side of a wrist with said shun spot being on a heart side, said khan spot being between said heart side and a distal end side, and said shaku spot being on said distal end side.

* * * * *